United States Patent
Olafsson et al.

(10) Patent No.: US 9,572,689 B2
(45) Date of Patent: Feb. 21, 2017

(54) KNEE ROTATIONAL ADAPTER

(71) Applicant: OSSUR hf, Reykjavik (IS)

(72) Inventors: Sigurdur Olafsson, Reykjavik (IS); Gudni Ingimarsson, Reykjavik (IS); David Landry, Quebec (CA)

(73) Assignee: OSSUR hf, Reykjavik (IS)

( * ) Notice: Subject to any disclaimer, the term of this patent is extended or adjusted under 35 U.S.C. 154(b) by 0 days.

(21) Appl. No.: 14/175,507

(22) Filed: Feb. 7, 2014

(65) Prior Publication Data

US 2014/0222166 A1 Aug. 7, 2014

Related U.S. Application Data

(60) Provisional application No. 61/761,966, filed on Feb. 7, 2013.

(51) Int. Cl.
| | |
|---|---|
| *A61F 2/50* | (2006.01) |
| *A61F 2/64* | (2006.01) |
| *A61F 2/68* | (2006.01) |
| *A61F 2/76* | (2006.01) |

(52) U.S. Cl.
CPC . *A61F 2/64* (2013.01); *A61F 2/76* (2013.01); *A61F 2002/5018* (2013.01); *A61F 2002/5069* (2013.01); *A61F 2002/6854* (2013.01)

(58) Field of Classification Search
CPC ........ E05B 21/066; E05B 35/00; E05B 73/02; E05B 1/0038; E05B 1/0046; E05B 65/0805; A61F 2/64; A61F 2/76; A61F 2002/5016; A61F 2002/5021; A61F 2002/5038; A61F 2002/5039; A61F 2002/5041; A61F 2002/5043; A61F 2002/5075; A61F 2002/607; A61F 2002/6818; A61F 2002/6854; Y10T 403/599

USPC ............ 623/27, 31, 38, 41; 70/59, 62; 292/137–138, 140, 163–165, 169–170, 292/279, 359; 248/222.52; 403/46

See application file for complete search history.

(56) References Cited

U.S. PATENT DOCUMENTS

| | | | | |
|---|---|---|---|---|
| 1,428,810 | A | * | 9/1922 | Shoemaker ...................... 70/62 |
| 3,538,516 | A | | 11/1970 | Bailey et al. |
| 3,731,323 | A | * | 5/1973 | Glancy ......................... 623/27 |
| 4,023,215 | A | | 5/1977 | Moore |
| 4,520,512 | A | * | 6/1985 | Lehneis .................. A61F 2/60 623/39 |

(Continued)

FOREIGN PATENT DOCUMENTS

DE 202008002764 U1 7/2008

OTHER PUBLICATIONS

Fillauer Trans-Femoral Rotator. Vertified by the wayback machine Sep. 5, 2012. http://www.fillauer.com/Lower-Extremity-Prosthetics/index.html.*

(Continued)

*Primary Examiner* — Thomas J Sweet
*Assistant Examiner* — Christie Bahena
(74) *Attorney, Agent, or Firm* — Workman Nydegger (57) ABSTRACT

A prosthetic adapter including a lower connector, an upper connector rotatably coupled to the lower connector, and a locking mechanism for preventing the upper connector from rotating relative to the lower connector. The locking mechanism is arranged to generally automatically retain a locked position when the lower connector is rotated to an original, predetermined alignment. An activation member is connected to and arranged for operating the locking mechanism.

16 Claims, 10 Drawing Sheets

(56) References Cited

U.S. PATENT DOCUMENTS

| | | | |
|---|---|---|---|
| 4,795,474 A * | 1/1989 | Horvath | 623/27 |
| 4,865,611 A * | 9/1989 | Al-Turaiki | 623/38 |
| 4,988,361 A | 1/1991 | Cooper | |
| 5,092,902 A | 3/1992 | Adams et al. | |
| 5,443,521 A | 8/1995 | Knoth et al. | |
| 5,888,234 A | 3/1999 | Littig | |
| 6,123,732 A | 9/2000 | Gramnas | |
| 6,355,071 B1 | 3/2002 | Cheng | |
| 6,458,163 B1 | 10/2002 | Slemker et al. | |
| 6,852,131 B1 | 2/2005 | Chen et al. | |
| 6,905,519 B2 | 6/2005 | Swanson, Sr. | |
| 7,318,504 B2 | 1/2008 | Vitale et al. | |
| 7,351,367 B2 | 4/2008 | Swanson, Sr. | |
| 7,416,565 B1 * | 8/2008 | Al-Turaikl | A61F 2/60 623/52 |
| 2007/0173955 A1 | 7/2007 | Archer et al. | |
| 2007/0260328 A1 | 11/2007 | Bertels et al. | |
| 2009/0082869 A1 | 3/2009 | Slemker et al. | |
| 2009/0171470 A1 * | 7/2009 | Bisinger et al. | 623/43 |
| 2009/0192630 A1 | 7/2009 | Slemker et al. | |
| 2011/0009981 A1 | 1/2011 | Okuda et al. | |
| 2011/0270415 A1 | 11/2011 | Chen et al. | |
| 2012/0065742 A1 | 3/2012 | Wu | |
| 2012/0245707 A1 * | 9/2012 | Osgyan et al. | 623/32 |

OTHER PUBLICATIONS

Ottobock (p. 1 and 2) Rotation-Adapter. Ottobock Lower Extremity Prosthetics Catalog 2009.*
Scheck and Siress (p. 1 and 2): Rotators. www.scheckandsiress.com Jan. 27, 2006.*
Brochure: "Mauch Knee", 2 pages. Feb. 7, 2013.
Brochure: "Mauch Knee Systems Adjustments", 2 pages. Copyright 2009.
Manual: "Mauch Knee, Life Without Limitations", 8 pages. Feb. 7, 2013.
International Search Report and Written Opinion of the International Searching Authority from International Application No. PCT/US2014/015347, May 6, 2014.

* cited by examiner

KNEE ROTATIONAL ADAPTER

TECHNICAL FIELD

The present disclosure relates to a prosthetic device for providing selective rotation to a prosthetic limb about its longitudinal axis.

BACKGROUND

Prosthetic devices provide amputees means for having a normal quality of life. Prosthetic devices are especially beneficial for transfemoral amputees, in which their amputation extends above the knee. For these individuals, a conventional above-the-knee prosthetic device may include a lower portion, such as an artificial lower leg and foot, and an upper portion, such as a rigid socket used for securing to the amputee's residual limb. A knee joint may be used to connect the lower and upper portions, and provide mobility to an amputated leg.

An artificial knee joint is typically connected between the upper and lower portions of the above-the-knee prosthesis to swing the lower portion relative to the upper portion to facilitate walking. Conventional artificial knee joints provide the same functionality as a normal knee and may include a hydraulic system with a pneumatic or spring cylinder. These systems generate a resistance or drag force to perform the swing motion of the lower leg during walking. Some artificial knees also require an additional attachment means to connect the knee joint to either the upper and/or lower prosthesis portion.

Figure 1:
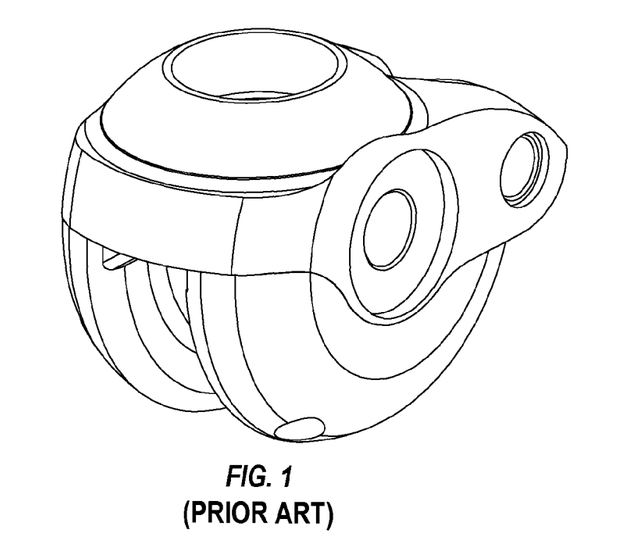
FIG. 1 is a perspective view of a conventional prosthetic knee adapter.

FIG. 1 shows an example of a customary adapter for connecting an upper portion of a transfemoral prosthesis to a lower portion. Such adapters are limited because they can only provide flexion and extension to a transfemoral prosthesis, and permit no twisting motion. The ability to achieve full use of a prosthetic limb is an important factor in both the physical and mental rehabilitation of an amputee. Allowing an amputee to operate their prosthetic device as if it was a normal limb is important during both walking and sitting.

Classic single-axis prosthetic knees only allow slight swinging of the lower portion of the leg prosthesis to mimic the wearer's natural gait. However, a true recreation of the gait cycle requires more than just bending at the knee. It would also require proper flexion and coordination between the ankle and hip as well. Attempts to more closely recreate a true gait motion by altering prosthetic knees to include additional axes from which to rotate about during ambulation have resulted in dangerous conditions. Allowing the lower portion of an above-the-knee prosthesis to rotate about its longitudinal axis while walking creates the risk of twisting an attached prosthetic foot out of proper stepping alignment. This leads to an unstable and unsafe walking motion.

When an amputee walking on an uneven surface tries to stop, the amputee will fall down if the artificial knee joint cannot resist rotation. It is important to maintain both dynamic and static alignment of the lower and upper portions of the above-the-knee prosthetic device in order to properly stabilize rotation of the lower portion from the upper portion when walking or standing still.

There are other times apart from ambulation when an amputee may want to rotate the lower portion of the transfemoral prosthesis about its longitudinal axis. The ability to twist the lower portion could allow the wearer to sit cross-legged on the ground, such as in a lotus position. Conventional knee joints in above-the-knee prostheses do not permit this type of rotation since their main purpose resists such twisting to ensure a steady and predictable bending motion during walking.

It can be seen from the foregoing there are many substantial needs for improving on the drawbacks of conventional prosthetic knee adapters. The present disclosure addresses these aforementioned shortcomings.

SUMMARY

The knee rotational adapter described is configured for use with a transfemoral prosthesis for above-the-knee amputees. The same concepts and methods described may be similarly used for other prosthetic devices and are not limited solely to the anatomical locations discussed.

An objective of the present disclosure to provide an improved prosthetic rotational knee joint adapter permitting adequate pivoting of the lower portion of a transfemoral prosthesis relative to the upper portion for stable walking, yet also allowing the user to selectively rotate the lower portion of the prosthesis as desired.

It is another objective of the present disclosure to provide a knee joint adapter for releasable interconnecting an upper and lower portion of an above-the-knee prosthetic leg that can be rotated from a predetermined normal position about its longitudinal axis as desired and selectively locked in place to prevent unwanted rotation when walking.

There is a clear need to provide an easy, quick and reliable way of adjusting the axial alignment of a lower portion of a transfemoral prosthesis.

The knee rotational adapter of the present disclosure is configured for attachment to a lower portion of the transfemoral prosthesis, such as an artificial knee joint connected to an artificial lower leg. The knee rotational adapter is for attaching to an upper portion of the above-the-knee prosthesis, such as a rigid socket fastened to the amputee's residual limb. This arrangement keeps the knee rotational adapter secured between the upper and lower portions of the transfemoral prosthesis.

The knee rotational adapter of the present disclosure can releasably interconnect the upper and lower portions of a transfemoral prosthesis. Placing the knee rotational adapter between the upper and lower portions further permits the lower portion to be rotated about its longitudinal axis as desired while the upper portion remains rigidly secured to the amputee. Allowing the lower portion of the transfemoral prosthesis to twist about its longitudinal axis relative to the upper portion gives the amputee the ability to sit cross-legged, such as in the lotus position.

A locking means is preferably provided on the knee rotational adapter to prevent any unwanted axial rotation of the lower portion when walking. Selectively restricting such twisting helps to maintain a steady and predictable bending motion during walking caused solely by the flexion and extension afforded by the lower portion of the transfemoral prosthesis, such as the artificial knee connected to the adapter.

The knee rotational adapter of the present disclosure can maintain adequate mechanical strength to withstand the static and variable loads to which the transfemoral prosthesis is subjected and they should not adversely affect the amputee's gait pattern. The knee rotational adapter is preferably constructed to withstand large tilting forces since it must bear the entire weight of the amputee to offer as much natural mobility as possible. Preventing axial rotation of a knee joint is necessary to ensure safe and stable operation of the lower limb when walking. Maintaining a proper knee center while walking by prohibiting axial rotation of the adapter can help discourage knee disarticulations.

In an embodiment, the prosthetic adapter includes a lower connector and an upper connector rotatably coupled to the lower connector. The adapter has a locking mechanism for preventing the upper connector from rotating relative to the lower connector. The locking mechanism is arranged to generally automatically retain a locked position when the lower connector is rotated to an original, predetermined alignment relative to the upper connecter. An activation member connects to and is arranged for operating the locking mechanism.

The locking mechanism may include a housing generally located at a top surface of the lower connector, and includes a locking member and at least one guide member arranged to receive the locking member. The locking member may be arranged to be urged into a locked position via an elastic return member in relation to the upper connector. The upper connector may form a stop detent on a base thereof. The locking member may be arranged to selectively engage the stop detent. The activation member may include a lock cap secured to the locking member so the lock cap moves with the locking member from a locked position to an unlocked position.

The adapter may include a release mechanism having an actuator coupled to and arranged for driving the activation member from a first position to a second position. The activation member may be configured to automatically return to the first position upon release of the release mechanism.

The adapter may include a first bearing ring connected between the upper connector and the frame. The lower connector may define a recess arranged for receiving the first bearing ring.

The adapter can have a retaining cap extending through a first receiving hole defined by the lower component and a second receiving hole defined by the upper connector from a first direction. A securing member may secure to the retaining cap and extends into the first receiving hole from a second direction. A second bearing ring is provided between the retaining cap and the upper connector, and is arranged to permit rotational movement of the lower connector relative to the upper connector when the retaining cap is adjusted.

In a variation, an actuator is arranged as an outer adjustment ring attached to the upper connector and connects to the activation member for selective engagement of the locking mechanism. The locking mechanism includes a locking member and the activation member engages the locking member. An elastomeric return member engages the activation member for automatically returning the locking member to a locked position. A stop detent is preferably located on the outer periphery of a top surface of the lower connector and configured for engagement with the locking member. The locking mechanism further comprises a guide member on a periphery of the base portion of the upper connector for guiding the locking member into proper alignment with the stop detent as it is moved between a locked and an unlocked position.

The adapter may be included in a prosthetic knee assembly including a knee joint for providing flexion and extension to upper and lower leg prostheses. A lower component pivotally connects the adapter to the knee joint. The adapter is arranged to connect to an upper leg prosthesis.

Methods are envision and are apparent from this disclosure for providing an amputee having a prosthetic knee assembly with rotational movement.

These and other features, aspects, and advantages of the present disclosure will become better understood regarding the following description, appended claims, and accompanying drawings.

The figures are not necessarily drawn to scale, but instead are drawn to provide a better understanding of the components, and are not intended to be limiting in scope, but rather to provide exemplary illustrations. The figures illustrate exemplary embodiments of a knee rotational adapter and the components, and in no way limit the structures or configurations of a knee rotational adapter and components according to the present disclosure.

DETAILED DESCRIPTION OF VARIOUS EMBODIMENTS

A. Overview

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings and are described below. There is no intention to limit the disclosure to the specific embodiments described, but on the contrary, the intention covers all modifications, alternative constructions, combinations, and equivalents falling within the spirit and scope of the disclosure.

Unless a term is expressly defined in this disclosure to possess a described meaning, there is no intent to limit the meaning of such term, either expressly or indirectly, beyond its plain or ordinary meaning.

B. Environment and Context of the Various Embodiments

The knee rotational adapter described is configured for use with a transfemoral prosthesis for above-the-knee amputees. The same concepts and methods described may be similarly used for other prosthetic devices and are not limited solely to the anatomical locations discussed.

Using an artificial knee joint is meant to provide functionality to an amputee similar to that of a normal knee. The primary movements allowed by such artificial knee joints comprise flexion and extension of the transfemoral prosthesis. Flexion is accomplished by bending the knee joint and includes rearward rotational movement of the lower portion relative to the upper portion. Conversely, extension includes forward rotational movement of the lower portion relative to the upper portion. These movements allow the lower portion to swing relative to the upper portion to mimic the human gait cycle and facilitate walking.

General anatomical terms for the human body may be used for describing particular locations of the elements of the knee rotational adapter in comparison to the human body.

The terms "proximal" and "distal" refer to areas on the prosthetic socket that correspond to a location relative to where a residual limb can be inserted. For instance, the proximal end of the socket is its open end where a residual limb is inserted into. The distal end of the socket is defined by its closed end where the tip of the residual limb rests inside.

The terms "upper" and "lower" are commonly used to distinguish the part of the adapter that connects to an upper and lower prosthesis, respectively. The terms "top" and "bottom" are meant to represent a surface of the adapter in the superior and inferior directions, respectively, on an amputee's coronal or sagittal plane. Similarly, the terms "front" and "rear" are used to refer to the portion of the adapter directed toward the anterior and posterior directions, respectively, along an amputee's transverse plane.

The terms "lateral" and "medial" are relative terms generally understood as indicating location regarding the mid-saggital plane or midline. Therefore, elements that are located near the midline are referred to as "medial" and those elements further from the midline are considered to be "lateral."

C. Embodiments of the Knee Rotational Adapter

Figure 2:
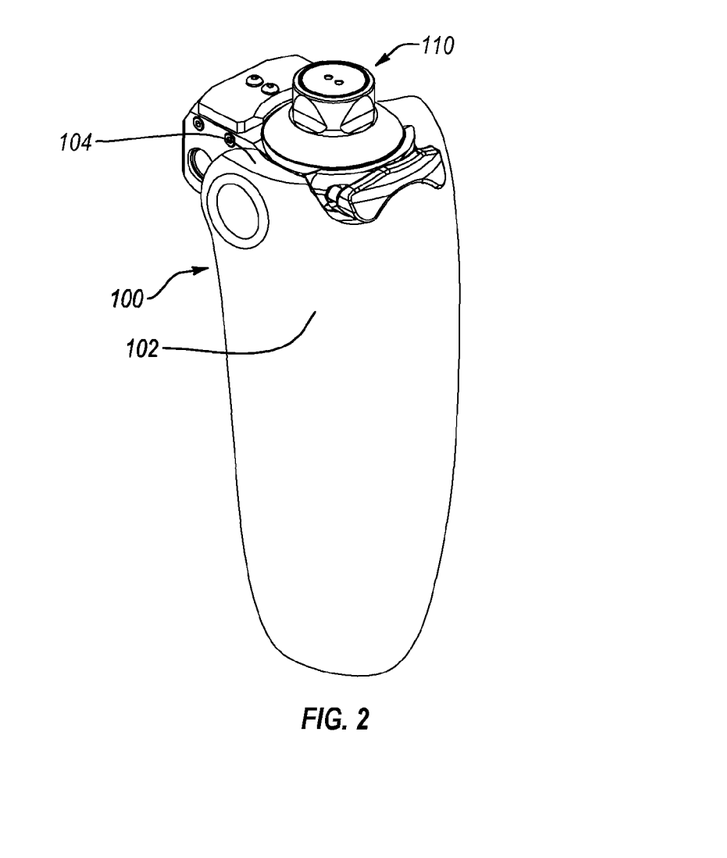
FIG. 2 is a perspective view of a knee rotational adapter secured to an artificial knee.

In accordance with a first embodiment of the disclosure as illustrated in FIG. 2, a prosthetic adapter 110, such as a knee rotational adapter, is configured for attachment to an artificial knee joint 100, such as a Mauch® Knee manufactured by Össur hf of Reykjavik, Iceland. Examples of such an artificial knee joint may be found in U.S. Pat. Nos. 5,092,902 and 5,443,521, each incorporated by reference.

The knee rotational adapter 110 can attach to various types of transfemoral prostheses that comprise an artificial knee joint. The knee rotational adapter 110 is secured within a casing 102 at a proximal or upper end 104 of the knee joint 100 opposite a distal or lower end 106. The knee rotational adapter 110 is pivotally attached to the knee joint 100 so it can provide both flexion and extension to the lower portion of a transfemoral prosthesis.

Figure 3:
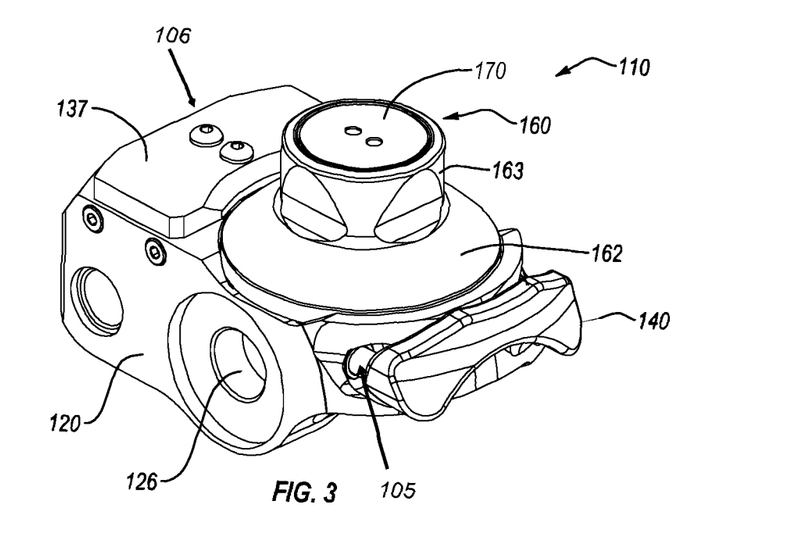
FIG. 3 is a perspective view of an embodiment of the knee rotational adapter of the present disclosure.
Figure 4:
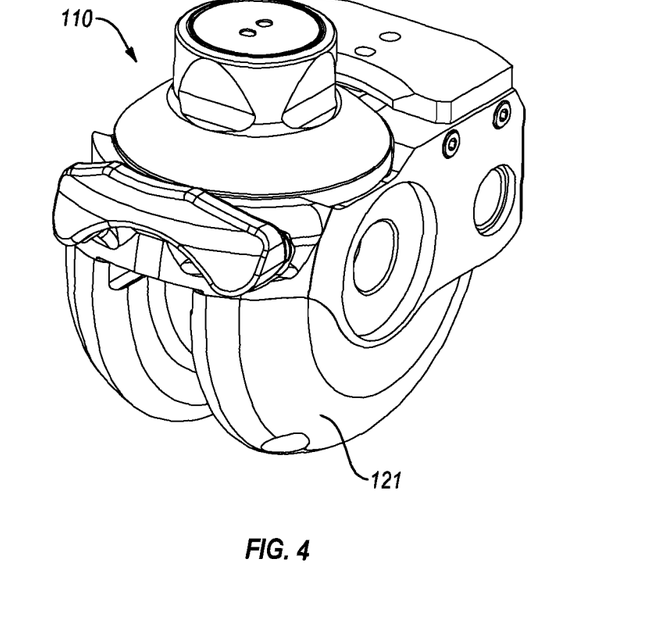
FIG. 4 is a perspective view of the knee rotational adapter according to the embodiment of FIG. 3 further comprising a femoral component.
Figure 5:
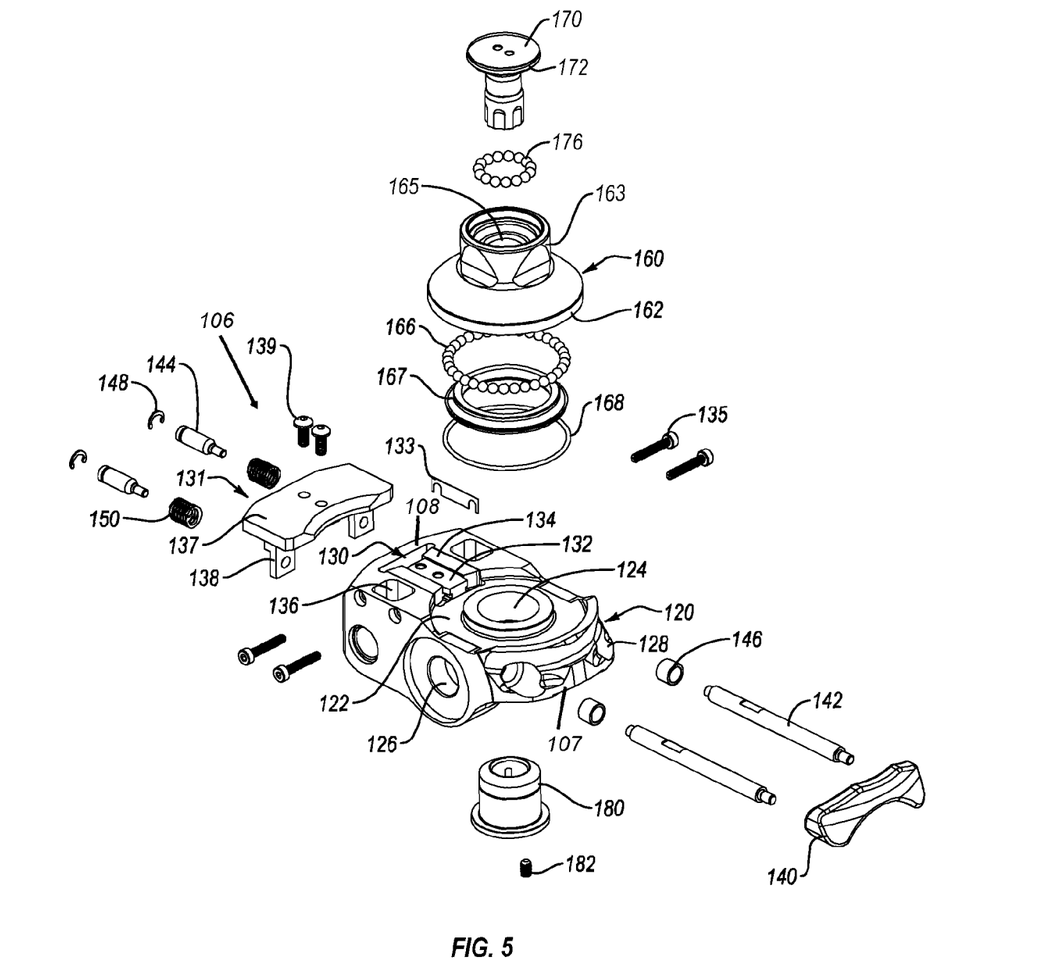
FIG. 5 is an exploded view of the knee rotational adapter of FIG. 3.

The knee rotational adapter 110 is shown in greater detail in FIGS. 3-5. The adapter 110 comprises a lower connector 120 acting as a frame, wherein the lower connector and frame are used interchangeably as the same feature according to the embodiment, having a top and bottom surface, a first portion 107 and a second portion 108, and a lateral and medial surface configured for attachment to a lower portion of the transfemoral prosthesis, such as an artificial knee. The adapter 110 further comprises a generally dome-shaped upper connector 160 rotatably coupled to the top surface of the frame 120 and configured for attachment to an upper portion of the transfemoral prosthesis, such as a socket or other mounting means.

The top surface defines a substantially circular recess 122 for receiving a correspondingly shaped base portion 162 of the upper connector 160. A first receiving hole 124 that is concentrically aligned within the recess 122 extends from the top surface to the bottom surface of the frame 120. At least one of the lateral or medial surfaces further defines a pivot hole 126 for pivotally connecting to an artificial knee joint to provide flexion and extension to the transfemoral prosthesis. Further, the bottom surface of the frame 120 may optionally be provided with a lower or femoral component 121 defining both lateral and medial condylar portions.

The knee rotational adapter 110 preferably includes a locking mechanism 106 movably attached to the lower connector 120 to prevent it from rotating relative to the upper connector 160. Such a locking mechanism 106 advantageously prohibits an amputee from twisting the frame 120 and the corresponding lower portion of the transfemoral prosthesis connected thereto relative to the upper connector 160 when in a locked position. The locking mechanism 106 is designed to automatically assume and retain a locked position when the frame 120 is rotated to its original alignment. The adapter 110 comprises a release mechanism 105 secured to the frame 120 for manipulating the locking mechanism 106 from a locked position to an unlocked position. This provides rotational adjustability to a user when desired, such as for crossing legs when sitting down.

The locking mechanism 106 comprises a housing 130 on the top surface of the frame 120 that includes a locking member 132 and at least one guide member 134. The locking member 132 acts as a plunger that can be urged into a locked position via an elastomeric return member 150, such as a compression spring.

Figure 6:
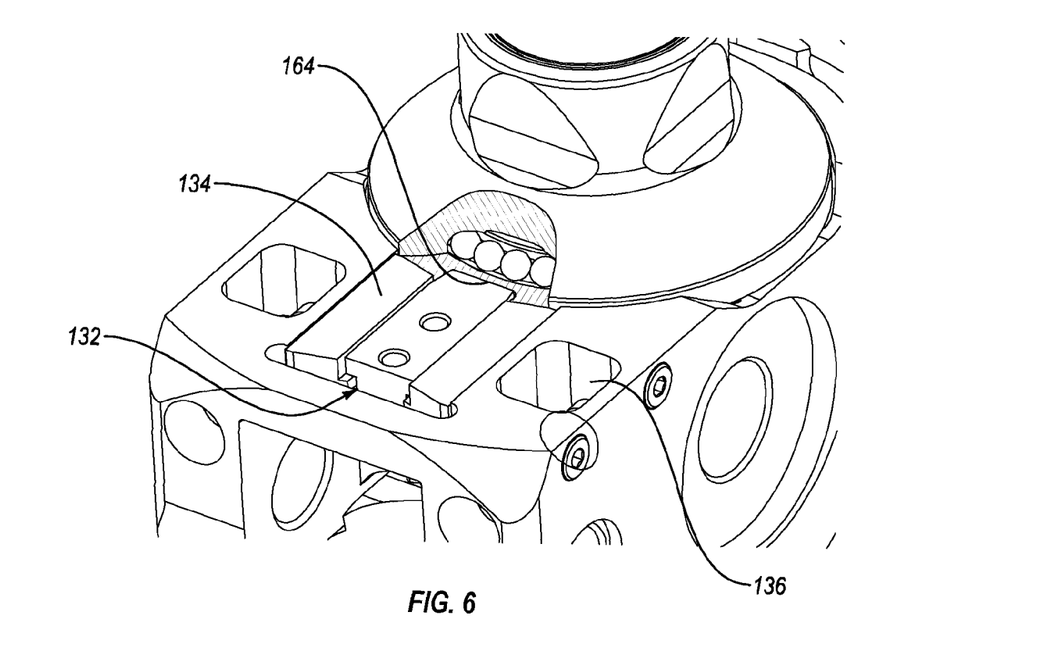
FIG. 6 is a perspective view of the locking member of the knee rotational adapter configured in a locked position.
Figure 7:
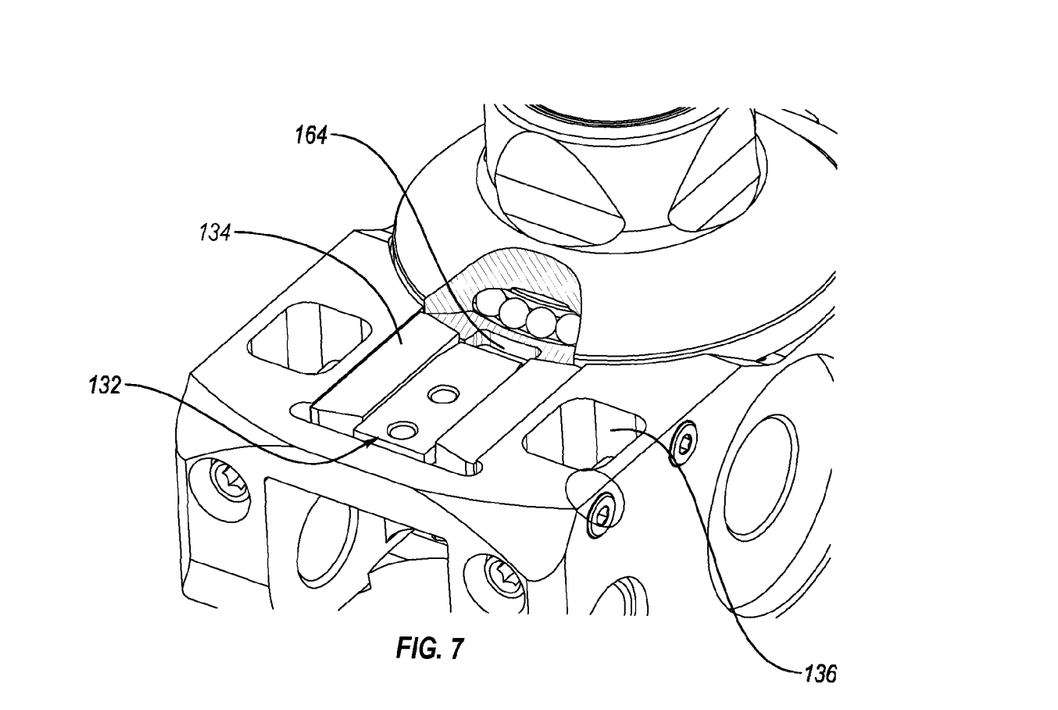
FIG. 7 is a perspective view of the locking member of the knee rotational adapter configured in an unlocked position.

Referring to FIGS. 6 and 7, when in the locked position, an engagement end of the locking member 132 engages a corresponding stop detent 164 formed on the base portion 162 of the upper connector 160 as shown in FIG. 6. The engagement end of the locking member 132 is preferably tapered for wedging within the stop detent 164 to minimize or prevent a loose fit. The at least one guide member 134 serves as a lock slide and defines a protrusion for mating with a corresponding slit formed on the locking member 132, which helps secure the locking member to the frame 120. This arrangement also guides the locking member as it is moved in and out of a locked position within the housing 130. FIG. 7 shows the locking member 132 disengaged from the stop detent 164 in an unlocked position.

At least one slide fastener 135, such as a threaded screw, can be inserted through a hole on the lateral or medial surface of the frame 120 to secure the guide member 134 within the housing 130. The locking mechanism 106 further comprises an activation member 131 operably connected to the locking member 132. The activation member 131 includes a lock cap 137 rigidly secured to the locking member 132 by at least one cap fastener 139, such as a threaded screw, so the lock cap 137 can respectively move with the locking member 132 from a locked position to an unlocked position.

At least one trigger 138 extends from a bottom surface of the lock cap 137 such that when the lock cap is secured to the locking member 132, the at least one trigger rests within a corresponding guide cavity 136 formed on the top surface of the frame 120 adjacent to the housing 130. The at least one trigger 138 is arranged within the guide cavity 136 for engagement with the release mechanism 105.

Referring to FIG. 5, the release mechanism 105 comprises at least one driver for coupling the activation member 131 to an actuator 140, such as a push button. The at least one driver comprises a first and second push rod 142, 144. The first push rod 142 can be operably connected at a first end to the actuator 140. The adapter frame 120 further comprises at least one guide hole 128 extending from a front surface of the frame to a rear surface of the frame for housing the release mechanism 105. An opposite second end of the first push rod 142 is inserted into the corresponding guide hole 128 from the front of the frame 120, with a guide bushing 146. The second end of the first push rod 142 is adapted to engage the corresponding trigger 138 situated within the guide cavity 136.

The guide cavity 136 is preferably large enough to allow the trigger 138 to move within from a first location representing a locked position of the locking member 132 to a second location representing an unlocked position. When a user operates the actuator 140, the first push rod urges the attached trigger 138 within the guide cavity 136 in the direction toward the rear surface of the frame 120.

A stop member adapted to abut the front surface of the frame 120 may be on the actuator 140 to prevent the actuator from being pushed too far. This movement compresses the return member 150 between the trigger 138 and the rear inside wall of the guide cavity 136, which causes the lock cap 137 to also move toward the rear surface of the frame. The locking member 132 consequently disengages the stop detent 164 to unlock the frame 120 from rotating relative to the upper connector 160 as the lock cap 137 is shifted away from it. The position of the activation member 131 can serve as a visual indicator to let the amputee know whether the knee rotational adapter 110 is locked.

The second push rod 144 is further shown connected to the return member 150 and is preferably inserted into the corresponding guide hole 128 from the rear of the frame so a first end defining a male portion can mate with a matching female portion formed on the second end of the first push rod 142. The female and male portions of the first and second push rods, respectively, are preferably threaded to provide a secure yet detachable connection. At least one snap ring 148, such as a c-clip, may be attached to a second opposite end of the second push rod 144 for anchoring the release mechanism 105 to the frame 120.

The return member 150 is secured over the second push rod 144 within the guide cavity 136 so the first push rod 142 cannot urge the trigger 138 toward the rear of the frame 120 unless the actuator 140 is activated. Instead, the return member 150 will automatically decompress in order to return to its original non-deformed shape, thus pushing the trigger 138 within the guide cavity 136 in the direction toward the front of the frame 120. This results in moving the locking member 132 toward the base 162 of the upper connector 160 so it can engage the stop detent 164 formed thereon when the frame 120 is rotated back to its original position, and wherein the stop detent 164 is aligned with the locking member 132.

A lower bearing ring 166 and matching bottom race 167 are preferably attached to the base portion 162 of the upper connector 160 to enable the connector to rotate within the recess 122 of the frame 120. The upper connector 160 includes a second receiving hole 165 centrally extending through its longitudinal axis. A retaining cap or main stud 170 may be inserted into the neck portion 163 of the upper connector 160 so a mating end thereof extends through the second receiving hole 165 and partly into the first receiving hole 124 of the frame 120.

A securing member 180 is inserted into the first receiving hole 124 from the bottom surface of the frame 120 and is adapted to mate with the retaining cap 170. At least one fastening member 182, such as a set screw, can affix the securing member to the retaining cap 170, which secures the upper connector 160 to the adapter frame 120. An upper bearing ring 176 is preferably provided between the retaining cap 170 and the neck portion 163 so rotational movement of the lower connector relative to the upper connector is not restricted when the retaining cap is axially tightened to the securing member 180. The securing member 180 may function as a radial bearing or bushing to provide guidance between the upper connector 160 and the frame 120 since there is only a small amount of diametral clearance between the upper connector 160 and the securing member 180.

The retaining cap 170 can act as a bearing adjustment screw to control the rotational friction of the bearings based on how tight it is secured to the frame 120. First and second elastomeric sealing members 168, 172, such as o-rings or rubber washers, may be provided for sealing engagement between the bottom race and the upper connector, and the retaining cap and the upper connector, respectively. A lock shim 133 may be provided for manipulating the locking member.

A variation of the at least one driver for coupling the activation member 131 to the actuator 140 may comprise an elongate unitary push rod extending at least through the length of the guide hole 128. A first end of the unitary push rod is attachable to the actuator 140, while a second opposite end is attachable to a snap ring 148, such as a c-clip. An intermediate portion of the elongate push rod is preferably coupled to the corresponding trigger 138 for driving the activation member 131. This action accordingly causes the locking member 132 to disengage with the stop detent 164 unlocking the lower connector 120 to allow for rotation relative to the upper connector 160.

In a variation of the prosthetic adapter of FIG. 5, the retaining cap or main stud may be formed as a stud and nut, rather than in the embodiment of FIG. 5 where in the retaining cap 170 or main stud is form as a screw and a nut. In the variation, the lock cap does not move relative to other components of the adapter, rather it is held stationary.

Figure 8:
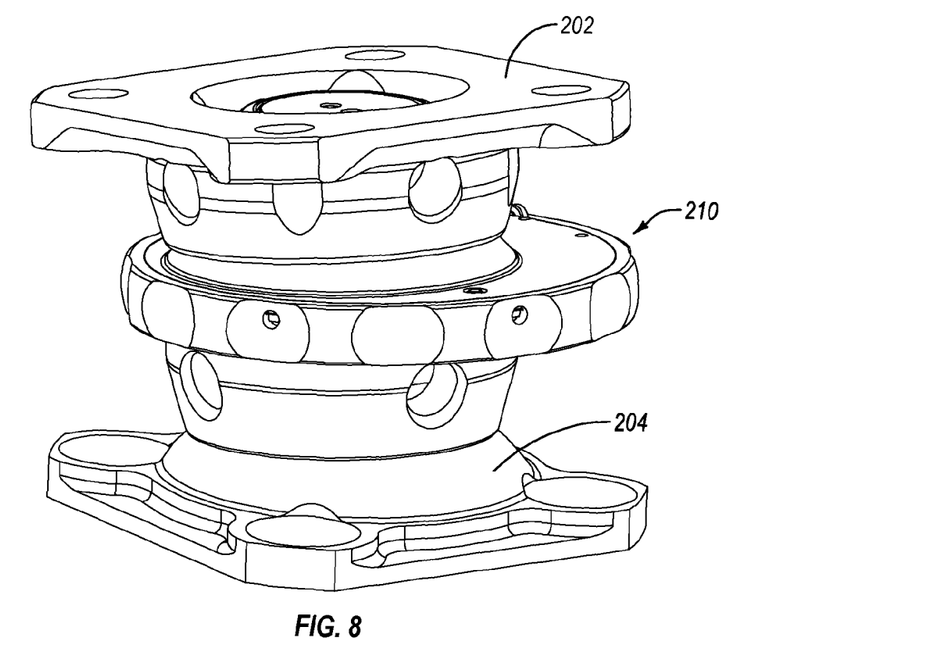
FIG. 8 a perspective view of another embodiment of the knee rotational adapter configured for attachment as a separate component between prosthetic members, such as upper and lower mounting plates.
Figure 9:
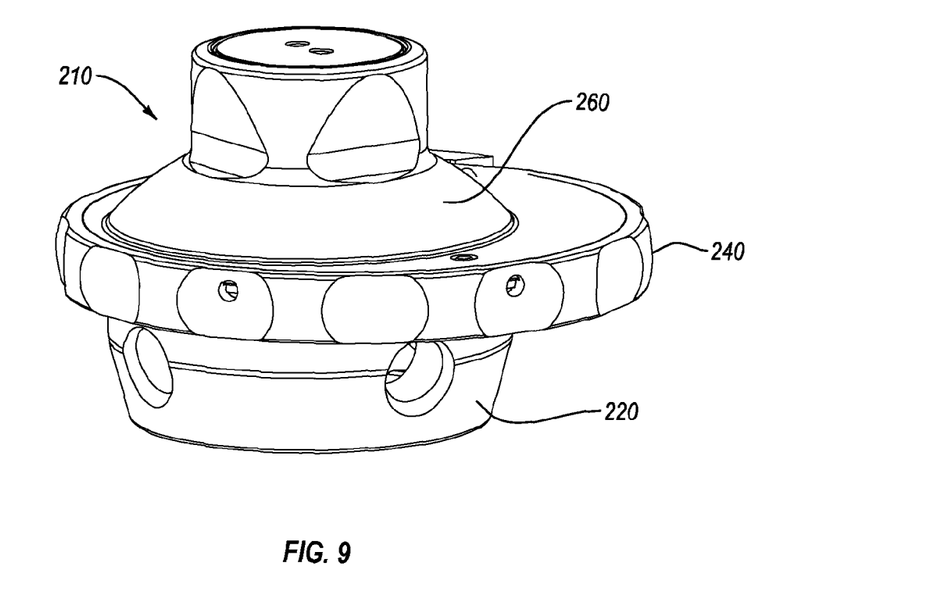
FIG. 9 is a perspective view of the knee rotational adapter according to the embodiment of FIG. 8.
Figure 10:
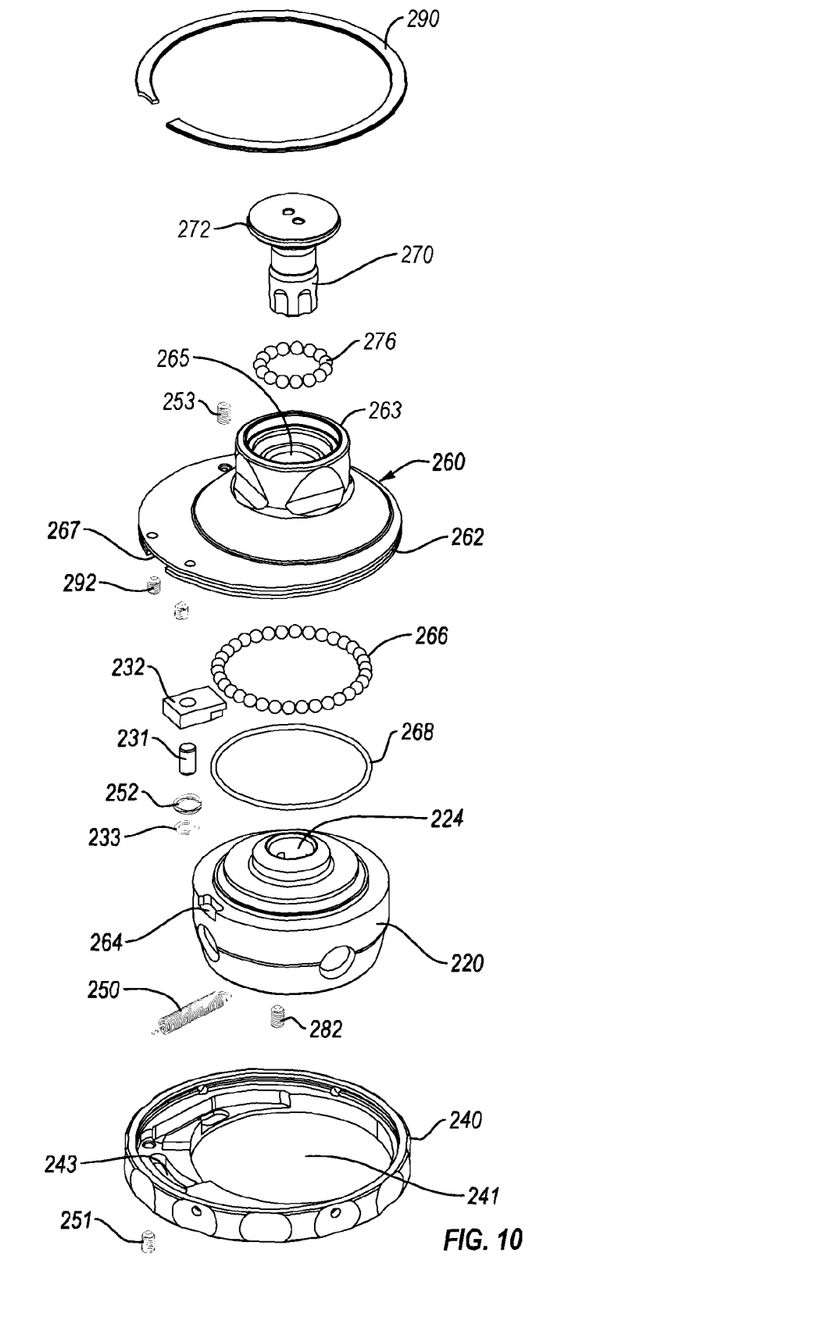
FIG. 10 is an exploded view of the knee rotational adapter according to the embodiment of FIG. 8.
Figure 11:
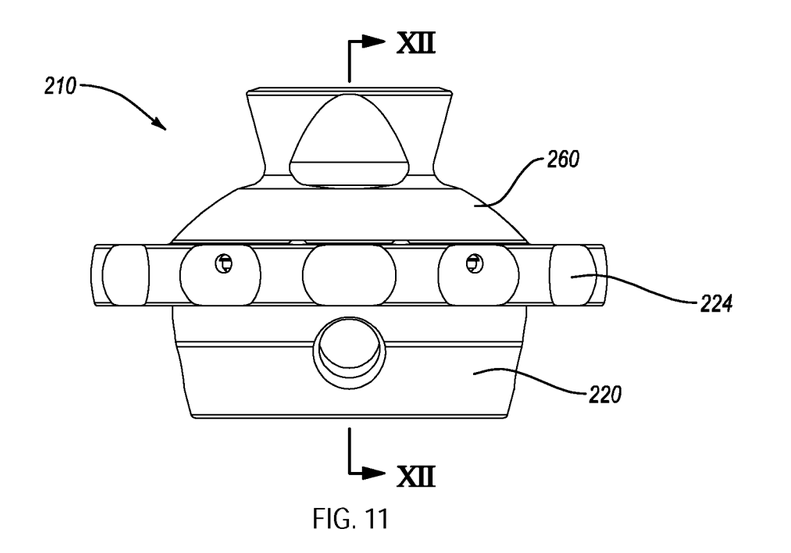
FIG. 11 is a side elevational view of the knee rotational adapter according to the embodiment of FIG. 8.
Figure 12:
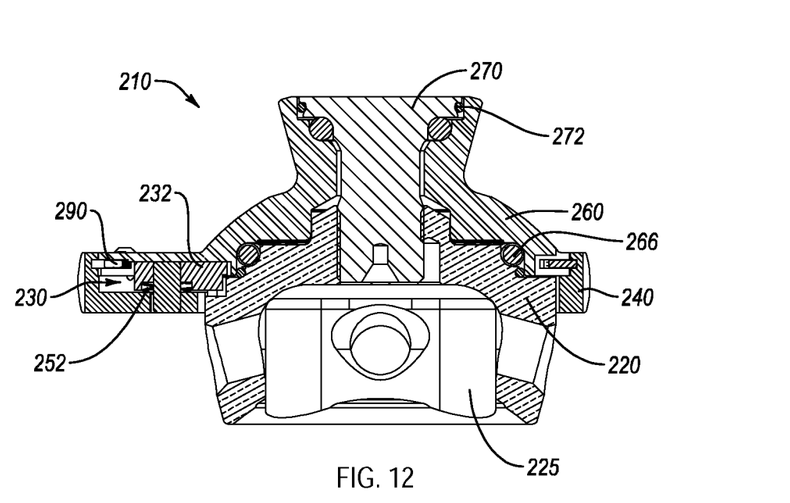
FIG. 12 is a side elevational view of a cross-section of the knee rotational adapter along the line XII-XII of FIG. 11.
Figure 13:
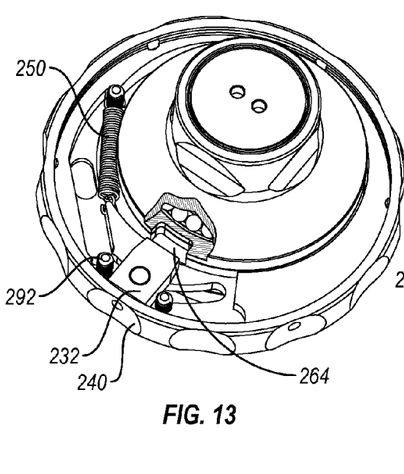
FIG. 13 is a top plan view of the knee rotational adapter according to the embodiment of FIG. 8 in a locked position.
Figure 14:
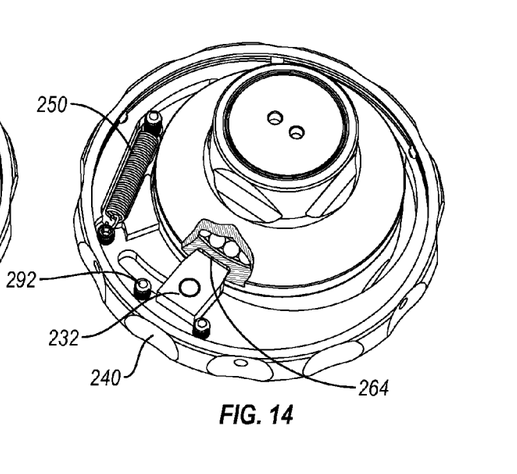
FIG. 14 is a top plan view of the knee rotational adapter according to the embodiment of FIG. 8 in an unlocked position.
Figure 15:
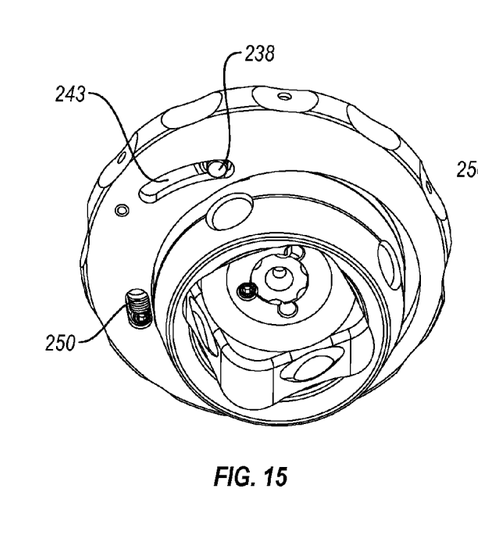
FIG. 15 is a bottom perspective view of the knee rotational adapter according to the embodiment of FIG. 8 in an unlocked position.
Figure 16:
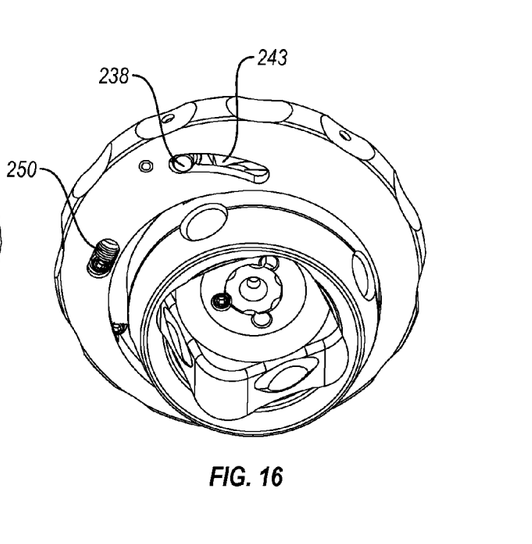
FIG. 16 is a bottom perspective view of the knee rotational adapter according to the embodiment of FIG. 8 in a locked position.
Figure 17:
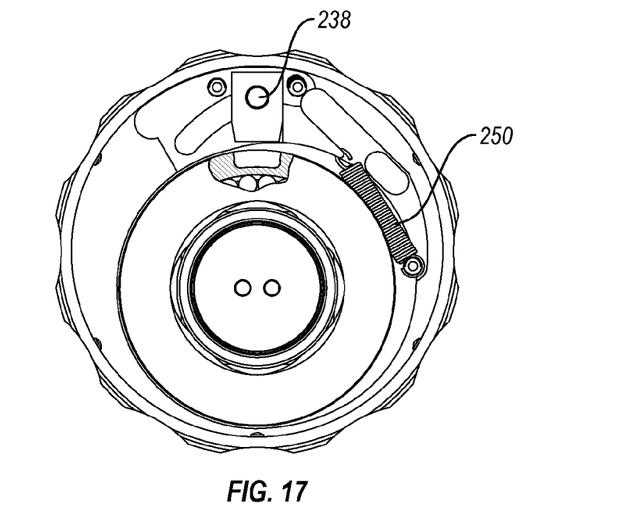
FIG. 17 is a bottom plan view of the of the knee rotational adapter according to the embodiment of FIG. 8.
Figure 18:
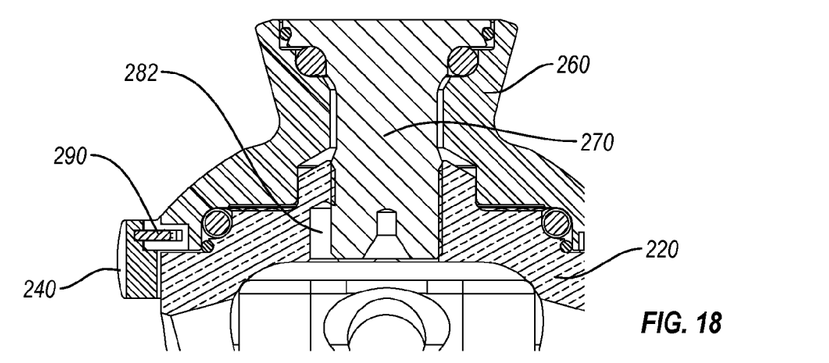
FIG. 18 is a partial cross-sectional view of the knee rotational adapter illustrating how a retaining cap can be used to secure an upper and lower connector to each other.

Referring to FIGS. 8 and 9, another embodiment of the knee rotational adapter 210 is shown for use as a separate component intended to be fitted between an artificial knee prosthesis and an upper leg prosthesis, such as a socket for receiving a residual limb. As depicted in FIG. 7, the knee rotational adapter 210 is secured between an upper and lower mounting plate 202, 204. Using the knee rotational adapter 210 as a separate component enables rotation of an artificial knee about an upper connector axis. It allows for free rotational movement when unlocked and may automatically lock against rotational movement when the rotating portions of the adapter are returned to an original alignment position.

Various types of locking mechanisms may be used with the knee rotational adapter to accomplish this. A user can easily access the knee rotational adapter during use to disengage the locking mechanism. This applies even when the user wears pants that would otherwise restrict or prevent the user from manipulating the locking mechanism since the knee rotational adapter of the present disclosure is easily accessible through such clothing.

FIGS. 8-18 exemplify an embodiment of the knee rotational adapter comprising an upper and lower connector 260, 220, a locking mechanism having an outer rotating ring with an eccentric opening, and a release mechanism. More particularly, the lower connector 220 includes a first receiving hole 224 centrally on a top surface and extending toward a bottom surface that defines a hollow cavity 225 configured for securing to a lower prosthesis or mounting plate. An upper connector 260 having a dome-shaped region and a substantially circular base portion 262 is configured for attachment to the top surface of the lower connector 220.

The upper connector 260 further includes a neck portion 263 extending from the dome-shaped region. The neck portion 263 defines a post for securing to an upper leg prosthesis, such as a socket, or mounting plate. The upper connector 260 also includes a second receiving hole 265 longitudinally extending through the neck portion 263. The neck portion 263 and corresponding dome-shaped region of the upper connector 260 are preferably not axially aligned with the center of the base portion 262. The first and second receiving holes 224, 265, however, should be in axial alignment when the lower and upper connectors 220, 260 are attached to each other.

A lower bearing ring 266 is preferably provided between the lower and upper connectors 220, 260 to ensure the lower connector 220 can rotate relative to the upper connector 260. The top surface of the lower connector 220 defines a grooved annular race for receiving said bearing ring. A first elastomeric sealing member 268, such as an o-ring or rubber washer, can be placed between the lower and upper connectors 220, 260 to provide a sealing engagement therebetween.

An actuator 240, such as a twistable outer adjustment ring having an easily gripable section, is provided for attachment to the bottom surface of the upper connector 260 and is operable to unlock the upper connector 260 from the lower connector 220 so the lower connector 220 can rotate freely relative to the upper connector 260. The actuator 240 is substantially circular and is adapted to receive the base portion 262 of the upper connector 260. The outer circumference of the base portion 262 defines a groove for receiving a coupling 290, such as a snap ring that serves as a clamping member. The coupling is further adapted to engage the upper connector 260 via at least one fastener 292, such as a set screw. When assembled, the outer edge of the clamping member 290 slightly protrudes from the base portion 262 to form a circumferential abutment about the perimeter of the upper connector 260.

An interior perimeter of the actuator 240 is configured to rotatably receive the abutting portion of the clamping member 290 for securing the actuator to the upper connector 260. The actuator also defines a non-concentric engagement hole 241 for receiving the lower connector 220. Placing the engagement hole 241 on the actuator defines a first eccentric region that laterally protrudes from the lower connector 220. The base portion 262 defines a second eccentric region that laterally protrudes from the top surface of the lower connector 220 when engaged therewith. These first and second eccentric regions form a housing 230 for a locking mechanism.

The locking mechanism comprises a locking member 232, such as a rectangular slide, an activation member 231, such as a control pin for manipulating the locking member, and an elastomeric return member 250, such as a tension spring for automatically returning the locking member to a locked position. A stop detent 264 is on an outer periphery of the top surface of the lower connector 220 and is configured for engagement with the locking member 232. The lower connector cannot rotate relative to the upper connector when the locking member engages the stop detent.

The locking mechanism further comprises a guide member 267 on a periphery of the base portion 262 of the upper connector 260 for guiding the locking member 232 into proper alignment with the stop detent 264 as it is moved between a locked and an unlocked position. The locking member 232 is adapted for attachment to the activation member 231. The activation member 231 is movably located within a curved guide channel 243 formed in the eccentric region of the actuator 240. Rotating the actuator 240 approximately 30 degrees in a counter-clockwise direction moves the activation member 231 from one end of the guide channel to the other end. This action disengages the locking member 232 from the stop detent 264 to allow for free rotation of the lower connector 220 relative to the upper connector 260.

The elastomeric return member 250 is preferably connected at one end to a first fastener 251, such as a set screw, secured directly to the actuator 240. The return member 250 is connected at its opposite end to a second fastener 253, such as a set screw, secured directly to the upper connector 260. As the actuator 240 is twisted to disengage the locking member 232 from the stop detent 264 on the lower connector 220, the return member 250 is correspondingly tensioned.

Upon releasing the actuator 240, the return member 250 naturally reverts back to its non-tensioned state, therefore also rotating the actuator 240 back to its original alignment with the lower and upper connectors 220, 260. This causes the locking member 232 to reassume a locked position by urging it to re-engage the stop detent 264. An elastomeric compression member 252, such as a wave spring, may be placed between the locking member 232 and the actuator 240.

A retaining cap 270 is preferably inserted through the top opening of the second receiving hole 265 on the neck portion of the upper connector 260 in order to axially secure the lower connector 220 to the upper connector 260. When the retaining cap 270 is secured in place, its top surface preferably lies flush with the top rim of the neck portion 263. At least one cap fastening member 282, such as a set screw, may be located within the hollow cavity 225 of the lower connector 220 for keeping the retaining cap 270 in place.

An upper bearing ring 276 is also preferably inserted into the second receiving hole 265 of the neck portion 263 to allow the upper connector 260 to rotate relative to the retaining cap 270. The retaining cap 270 can therefore act as a bearing adjustment screw to control the ease of rotation allowed by the bearing rings based on how tight it is secured to the frame 120. A second elastomeric sealing member 272, such as an o-ring or a rubber washer, may be provided between the retaining cap 270 and the neck portion 263 to provide a sealing engagement therebetween. A lock spring shim 233 may be provided adjacent to the elastomeric compression member 252.

Figure 19:
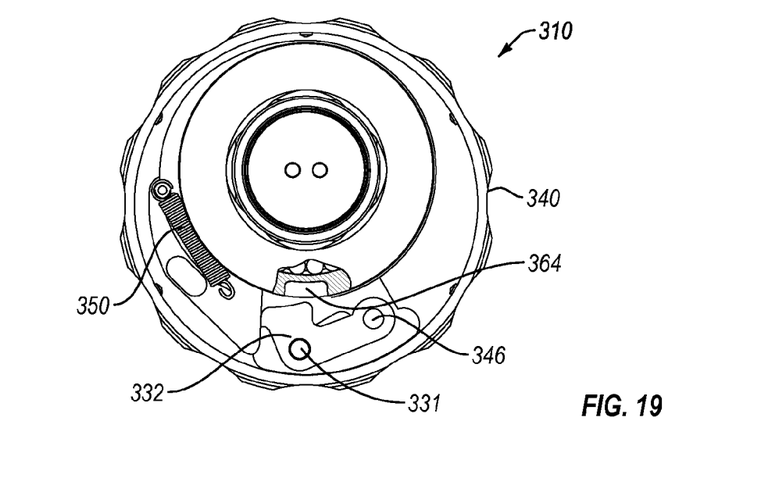
FIG. 19 is a perspective view of another variation of the knee rotational adapter.

FIG. 19 shows a variation of the knee rotational adapter 310 comprising a locking member 332 in a pivoting taper lock engageable at one end with the stop detent 364. Implementing such a pivoting taper lock within a housing allows the user to unlock the adapter by twisting an actuator 340 in a counter-clockwise direction. The actuator 340 may be an outer adjustment ring having an easily graspable section. The locking member 332 is configured for attachment to an activation member 331, such as a pin, moveably located within an elongated guide channel 343 formed in the eccentric region of the actuator 340. The locking member 332 is further configured at a second end for attachment to a pivoting member 346 on the actuator 340.

Sliding the activation member 331 away from the stop detent 364 causes the locking member 332 to correspondingly pivot away from the stop detent 364 for disengagement allowing the lower connector 220 to freely rotate relative to the upper connector 260. The shape of the taper lock helps to minimize or prevent a loose fit within the stop detent 364 in order to reliably maintain a locked position. The mating portion of the locking member 332 is preferably tailored to equally minimize the unlocking force on the lock when torque applies to the adapter. An elastomeric return member 350, such as a tension spring, may be provided for automatically returning the locking member back to a locked position when the actuator is released.

Figure 20:
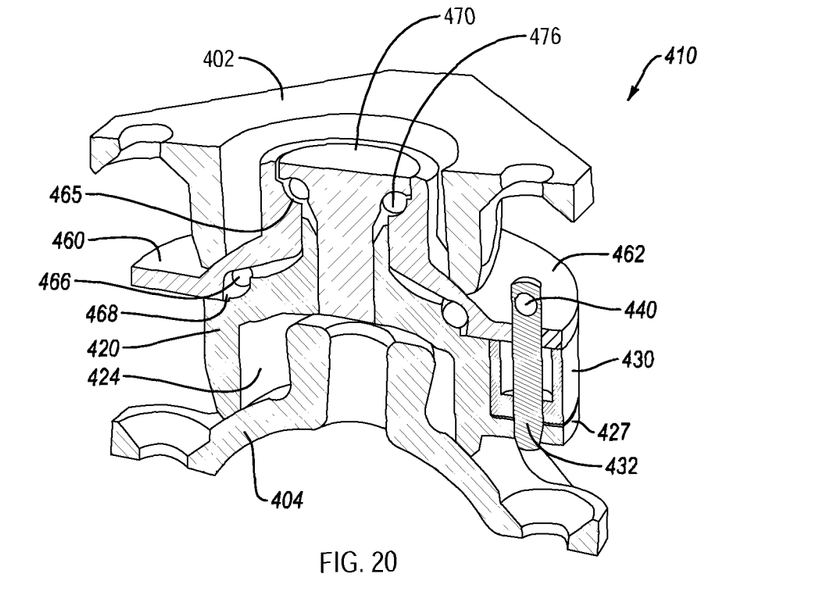
FIG. 20 is a perspective sectional view of another variation of the knee rotational adapter in a locked position connected to a pair of mounting plates.

FIG. 20 illustrates another variation of a knee rotational adapter 410 for use as a separate component and configured for attachment between an upper and lower mounting plate 402, 404. The knee rotational adapter 410 comprises a lower connector 420 having a first receiving hole 424 centrally on a top surface and extending toward a bottom surface that defines a hollow cavity for securing to the lower mounting plate 404. An upper connector 460 having a generally dome-shaped region and a substantially circular base portion is configured for attachment to the top surface of the lower connector 420.

The upper connector 460 further includes a neck portion extending from the dome-shaped region, and defining a post for securing to the upper mounting plate 402. The upper connector 460 also includes a second receiving hole 465 longitudinally extending through the center of the neck portion. Both the neck portion and corresponding dome-shaped region of the upper connector 460 are preferably concentrically aligned with the center of the base portion. The first and second receiving holes 424, 465 should be in axial alignment when the lower and upper connectors 420, 460 are mounted to each other.

A lower bearing ring 466 may be provided between the upper and lower connectors 420, 460 to ensure the lower connector 420 can rotate relative to the upper connector 460. The top surface of the lower connector 420 defines a grooved race for receiving said lower bearing ring 466. A first elastomeric sealing member 468, such as an o-ring or rubber washer, can be placed between the lower and upper connectors 420, 460 to provide a sealing engagement therebetween.

A locking mechanism comprising a locking member 432, such as a pin, may be provided for insertion into a housing 430 formed between the base portion of the upper connector 460 and a flange 427 extending radially outward from the lower connector 420. Corresponding openings in both the base portion and the flange 427 allow insertion of the pin 432. The knee rotational adapter 410 assumes a locked position when the pin 432 is firmly inserted within the housing 430 for engaging both the base portion and the flange 427, such that the lower connector 420 is prevented from rotating relative to the upper connector 460. A first end of the pin is preferably tapered to minimize play when engaged with the flange 427.

An actuator 440 may be on a second opposite end of the locking member for unlocking the knee rotational adapter. The actuator 440 may comprise a handle portion for attachment to a lanyard. The user can therefore easily pull said lanyard to slide the pin within the housing 430 and disengage the locking member from the flange 427.

The lower and upper connectors 420, 460 may be secured to each other via a retaining cap 470 that can be inserted through the top opening of the second receiving hole 465 on the neck portion of the upper connector. An upper bearing ring 476 is preferably inserted into the second receiving hole 465 of the neck portion to allow the upper connector 460 to rotate relative to the retaining cap. A second elastomeric sealing member 472, such as an o-ring or a rubber washer, may be provided between the retaining cap and the neck portion to provide a sealing engagement therebetween.

Figure 21:
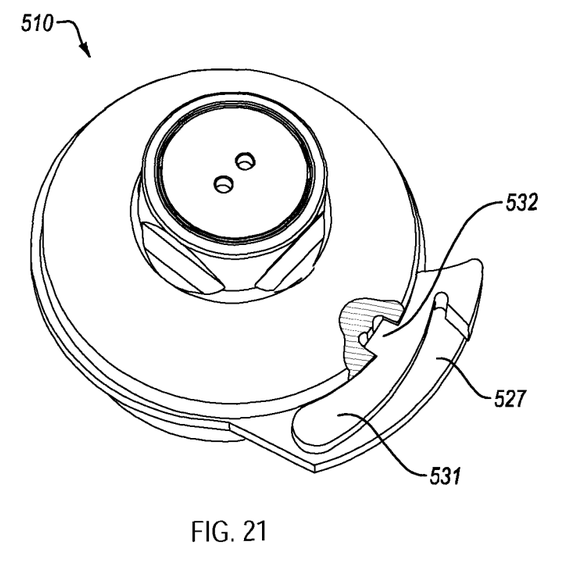
FIG. 21 is a perspective view of another variation of the knee rotational adapter in a locked position.

FIG. 21 shows another variation of a knee rotational adapter 510 comprising a lower and upper connector 520 and a locking mechanism for preventing free rotation of each connector. The locking mechanism comprises a flange 527 extending radially outward from a top surface of the lower connector 520, an activation member 531 such as a pivot arm configured at one end for pivotally attaching to the flange 527, and at least one stop detent formed on an outer periphery of the upper connector. The pivot arm 531, further comprises a locking member 532 formed thereon, and an opposite trigger end of the pivot arm is adapted for manipulating said locking member 532 in and out of engagement with the stop detent.

The locking member 532 is received within the stop detent to secure the knee rotational adapter in a locked position. The locking member may be disengageable from the stop detent. The locking member 532 is preferably tapered to prevent a loose fit when engaged with the stop detent. A user advantageously only needs to pull the trigger end of the locking member 532 a short radial distance away from the knee rotational adapter 510 to unlock it due to the proximity of the locking member 532 from the stop detent. Numerous stop detents can be formed on the upper connector to allow the knee rotational adapter 510 to be locked in a variety of positions.

While the foregoing embodiments have been described and shown, alternatives and modifications of these embodiments, such as those suggested by others, may be made to fall within the scope of the disclosure. While the knee rotational adapter has been described with a leg prosthesis, it will be understood that the principles described may be extended to other types of prosthetic devices.

The invention claimed is:

1. A prosthetic adapter, comprising: a lower connector having a first receiving hole, a first portion located on a first side of the first receiving hole, a second portion located on a second side of the first receiving hole, and a guide hole, the first and second portions located on opposite sides of the receiving hole in the transverse plane and arranged such that the guide hole extends from the first portion to the second portion; an upper connector rotatably coupled to the lower connector at the receiving hole; a locking mechanism, at the second portion of the lower connector, for preventing the upper connector from rotating relative to the lower connector, the locking mechanism arranged to automatically retain a locked position when the lower connector is rotated to an original, predetermined alignment relative to the upper connector; wherein the locking mechanism comprises at least a locking member; and an activation member connected to and arranged for operating the locking member; wherein the activation member is positioned at the second portion of the lower connector and arranged to serve as a visual indicator whether the locking mechanism is locked; a release mechanism located partially at the first portion of the lower connector; the release mechanism including a push rod and having an actuator coupled to and arranged for driving the activation member from a first position to a second position, wherein the activation member is configured to automatically return to the first position upon release of the release mechanism, the actuator located on the first portion of the lower connector and arranged to move relative thereto and urge the push rod from the first portion to the second portion of the lower connector through the guide hole formed by the lower connector, apart from the receiving hole, to move a position of the activation member.

2. The prosthetic adaptor of claim 1, wherein the locking mechanism includes a housing generally located at a top surface of the lower connector, and includes the locking member and at least one guide member arranged to receive the locking member.

3. The prosthetic adaptor of claim 2, wherein the locking member arranged to be urged into a locked position via an elastic return member coupled to the push rod in relation to the upper connector.

4. The prosthetic adaptor of claim 3, wherein the upper connector forms a stop detent on a base portion thereof, the locking member is arranged to selectively engage the stop detent.

5. The prosthetic adaptor of claim 2, wherein the activation member includes a lock cap secured to the locking member so the lock cap moves with the locking member from a locked position to an unlocked position.

6. The prosthetic adapter of claim 1, further comprising a first bearing ring connected between the upper connector and the lower connector.

7. The prosthetic adapter of claim 6, wherein the lower connector defines a recess arranged for receiving the first bearing ring.

8. The prosthetic adapter of claim 1, further comprising a retaining cap extending through a first receiving hole defined by the lower connector and a second receiving hole defined by the upper connector from a first direction, and a securing member secures to the retaining cap and extends into the first receiving hole from a second direction.

9. The prosthetic adapter of claim 8, further comprising a bearing ring provided between the retaining cap and the upper connector, and arranged to permit rotational movement of the lower connector relative to the upper connector when the retaining cap is adjusted.

10. The prosthetic adapter of claim 1, further comprising a stop detent located on the outer periphery of a top surface of the lower connector and configured for engagement with the locking member.

11. The prosthetic adapter of claim 10, wherein the locking mechanism further comprises a guide member on a periphery of a base portion of the upper connector for guiding the locking member into proper alignment with the stop detent as it is moved between a locked and an unlocked position.

12. A prosthetic knee assembly, comprising: a knee joint for providing flexion and extension to upper and lower leg prostheses, and connecting to a lower leg prosthesis; a prosthetic adapter connected to an upper end of the knee joint, the prosthetic adapter having lower and upper connectors, the upper connector rotatably secured to a lower connector at a receiving hole, the lower connector having a first portion located on a first side of the receiving hole, a second portion located on a second side of the receiving hole, and a guide hole, the first and second portions located on opposite sides of the receiving hole in the transverse plane and arranged such that the guide hole extends from the first portion to the second portion, the prosthetic adapter arranged for connection to an upper leg prosthesis; and a lower component pivotally connecting the adapter to the knee joint; a locking mechanism for preventing the upper connector from rotating relative to the lower connector, the locking mechanism arranged to automatically retain a locked position when the lower connector is rotated to an original alignment; wherein the locking mechanism comprises at least a locking member; and an activation member connected to and arranged for operating the locking member; wherein the activation member is positioned at the second portion of the lower connector and arranged to serve as a visual indicator whether the locking mechanism is locked; a release mechanism located partially at the first portion of the lower connector; the release mechanism including a push rod and having an actuator coupled to and arranged for driving the activation member from a first position to a second position, wherein the activation member is configured to automatically return to the first position upon release of the release mechanism, the actuator located on the first portion of the lower connector and arranged to move relative thereto and urge the push rod from the first portion to the second portion of the lower connector through the guide hole formed by the lower connector, apart from the receiving hole, to move a position of the activation member.

13. The prosthetic adaptor of claim 12, wherein the locking mechanism includes a housing generally located at a top surface of the lower connector, and includes the locking member and at least one guide member arranged to receive the locking member.

14. The prosthetic adaptor of claim 13, wherein the locking member is arranged to be urged into a locked position via an elastic return member in relation to the upper connector.

15. A prosthetic adapter, comprising: a lower connector having a first receiving hole, a first portion located on a first side of the receiving hole, a second portion located on a second side of the receiving hole, and a guide hole, the first and second portions located on opposite sides of the receiving hole in the transverse plane and arranged such that the guide hole extends from the first portion to the second portion; an upper connector rotatably coupled to the lower connector at the receiving hole; a locking mechanism, at the second portion of the lower connector, for preventing the upper connector from rotating relative to the lower connector, the locking mechanism arranged to automatically retain a locked position when the lower connector is rotated to an original alignment; wherein the locking mechanism comprises at least a locking member; and an activation member connected to and arranged for operating the locking member; wherein the activation member is positioned at the second portion of the lower connector and arranged to serve as a visual indicator whether the locking mechanism is locked; a release mechanism located partially at the first portion of the lower connector; the release mechanism including a push rod and having an actuator coupled to and arranged for driving the activation member from a first position to a second position, wherein the activation member is configured to automatically return to the first position upon release of the release mechanism, the actuator located on the first portion of the lower connector and arranged to move relative thereto and urge the push rod from the first portion to the second portion of the lower connector to move a position of the activation member.

16. The prosthetic adapter of claim 15, further comprising:
- a retaining cap extending through a first receiving hole defined by the lower connector and a second receiving hole defined by the upper connector from a first direction, and a securing member secures to the retaining cap and extends into the first receiving hole from a second direction;
- a first bearing ring connected between the upper connector and the lower connector;
- a second bearing ring provided between the retaining cap and the upper connector, and arranged to permit rotational movement of the lower connector relative to the upper connector when the retaining cap is adjusted.

* * * * *